United States Patent [19]

Morita et al.

[11] Patent Number: 4,985,430

[45] Date of Patent: Jan. 15, 1991

[54] 9-ACYLAMINO-TETRAHYDROACRIDINE DERIVATIVES AND MEMORY ENHANCING AGENT CONTAINING SAID DERIVATIVE AS ACTIVE INGREDIENT

[75] Inventors: Shuji Morita, Yokohama; Ken-Ichi Saito; Kunihiro Ninomiya, both of Machida; Akihiro Tobe, Yokohama; Issei Nitta, Machida; Mamoru Sugano, Kawasaki, all of Japan

[73] Assignee: Mitsubishi Kasei Corporation, Tokyo, Japan

[21] Appl. No.: 279,051

[22] Filed: Dec. 2, 1988

[30] Foreign Application Priority Data

Dec. 3, 1987 [JP] Japan ............................. 62-306753
Nov. 9, 1988 [JP] Japan ............................. 63-283351
Dec. 2, 1988 [JP] Japan ............................. 63-305799

[51] Int. Cl.$^5$ ................. A61K 31/505; A61K 31/435; A61K 31/495; C07D 401/12; C07D 219/08; C07D 221/18; C07D 221/16; C07D 221/16

[52] U.S. Cl. .............................. 514/253; 514/274; 514/255; 514/290; 514/291; 514/292; 514/297; 514/284; 514/285; 514/286; 514/293; 514/287; 514/289; 546/70; 546/74; 546/93; 546/97; 546/63; 546/61; 546/62; 546/64; 546/80; 546/81; 546/89; 546/102; 546/103; 546/104; 546/105; 546/106; 546/82; 546/83; 546/84; 544/316; 544/361

[58] Field of Search ................. 544/316, 361; 546/63, 546/64, 89, 104, 82, 70, 74, 93, 97; 514/274, 291, 284, 293, 253

*Primary Examiner*—John M. Ford
*Attorney, Agent, or Firm*—Oblon, Spivak, McClelland, Maier & Neustadt

[57] ABSTRACT

There are disclosed a 9-acylamino-tetrahydroacridine derivative represented by the following formula (I):

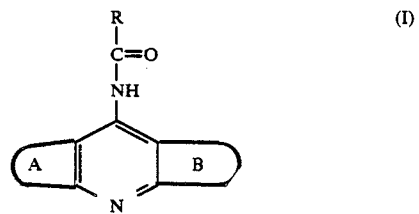

wherein R

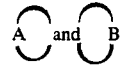

are as defined in the specification, its optical antipode or pharmaceutically acceptable acid addition salt thereof and a memory enhancing agent containing the same as an active ingredient.

10 Claims, No Drawings

9-ACYLAMINO-TETRAHYDROACRIDINE DERIVATIVES AND MEMORY ENHANCING AGENT CONTAINING SAID DERIVATIVE AS ACTIVE INGREDIENT

BACKGROUND OF THE INVENTION

This invention relates to a 9-acylamino-tetrahydroacridine derivative which is novel and available and which improves disfunction of cholinergic neurons, its optical antipode or pharmaceutically acceptable acid addition salt thereof, and a memory enhancing agent containing these compounds as an active ingredient.

As a therapeutic method of various memory disorder characterized by decreasing in cholinergic nervous function such as Alzheimer's disease, there exists an attempt to heighten a content of acetylcholine in brain using an acetylcholine esterase inhibitor. For example, an investigation using physostigmine has been reported in Neurology, Vol. 8, p. 377 (1978). Further, in publications of Japanese Provisional Patent Publications No. 148154/1986, No. 141980/1988, No. 166881/1988, No. 203664/1988, No. 225358/1988, No. 238063/1988 and No. 239271/1988; EP-A-268,871; and International Provisional Patent Publication No. 88/02256, there have been reported that specific 9-amino-tetrahydroacridine derivatives have acetylcholine esterase inhibiting functions and are effective for therapy of Alzheimer's disease. Also, there has been reported by Summers in "The New England Journal of Medicine, Vol. 315, p. 1241 (1986)" that 9-amino-1,2,3,4-tetrahydroacridine (tacrine) is effective to human Alzheimer's disease in combination with use of lecithin. However, the above methods involve problems that sufficient improvement has not yet accomplished or adverse reaction is caused whereby new therapeutic method has been desired.

On the other hand, as examples of known 9-acylamino-tetrahydroacridine, 9-acetylamino-tetrahydroacridine is described in "Journal of Chemical Society, p. 634 (1947)", and also 9-chloroacetylamino-tetrahydroacridine and 9- diethylaminoacetylamino-tetrahydroacridine are described in "Chem. listy, Vol. 51, p. 1056 (1957)" and also described that the latter has local anesthetic function. Further, in "Journal of Medicinal Chemistry, Vol. 18, p. 1056 (1975)", relationships in structural activity of acetylcholine esterase inhibiting function of 9-amino-tetrahydroacridine are described, and also described are activities of 9-acetylamino-tetrahydroacridine and 9-benzoylaminotetrahydroacridine become 1/1000 to that of 9-amino-tetrahydroacridine. Moreover, in the aforesaid patent publications (Japanese Provisional Patent Publications No. 166881/1988, No. 203664/1988, No. 225358/1988, No. 238063/1988 and No. 239271/1988), while 9-acylamino-tetrahydroacridine derivatives have been claimed, there is neither described in each of the publications concerning concrete synthetic examples nor pharmacological activities of the compounds having 9-acylamino group.

SUMMARY OF THE INVENTION

The present inventors have investigated intensive studies in order to provide a therapeutic agent for senile dimentia including Alzheimer's disease, and as the results, they have found that a specific 9-acylamino-tetrahydroacridine derivative, its optical antipode or pharmaceutically acceptable acid addition salt thereof become an agent for improving memory disorder such as Alzheimer's disease with a different mechanism from that of the conventional compound having acetylcholine esterase inhibiting function, whereby accomplished the present invention.

That is, the present invention comprises a 9-acylaminotetrahydroacridine derivative represented by the following formula (I):

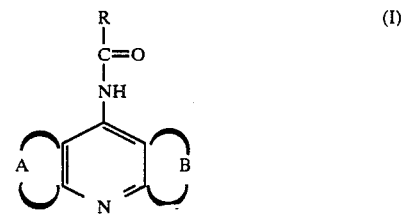

wherein R represents an alkyl group, an aralkyl group or the group represented by the formula (II):

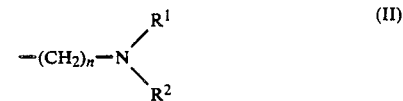

where $R^1$ represents a hydrogen atom or an alkyl group, $R^2$ represents a hydrogen atom,

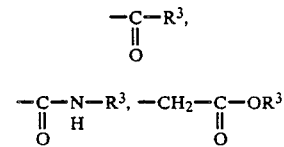

(where $R^3$ represents a hydrogen atom or an alkyl group) or

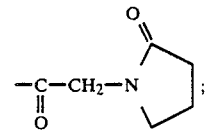

also, in the formula (II), the

may form

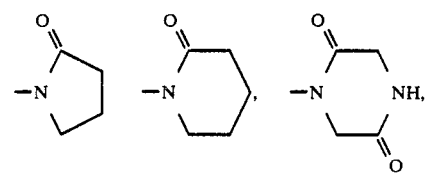

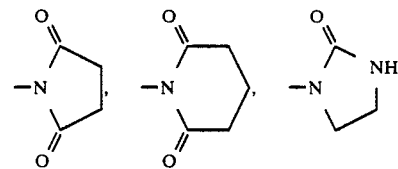

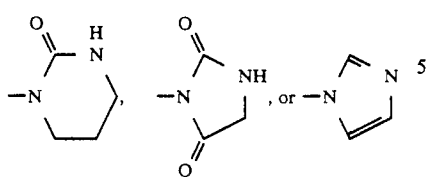

by combining $R^1$ and $R^2$ with each other; n represents 1 or 2;

represents

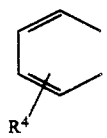

(where $R^4$ represents a hydrogen atom, a halogen atom, an alkyl group, an alkoxy group or a hydroxyl group) or

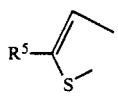

(where $R^5$ represents a hydrogen atom or an alkyl group); and represents

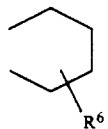

(where $R^6$ represents a hydrogen atom, an alkyl group or a hydroxyl group),

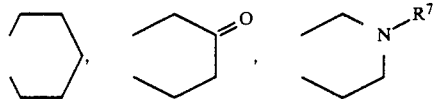

{where $R^7$ represents a hydrogen atom, an alkyl group, an aralkyl group,

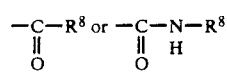

(where $R^8$ represents a hydrogen or an alkyl group)},

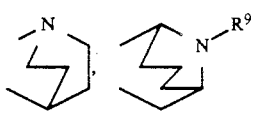

(where $R^9$ represents a hydrogen atom or an alkyl group),

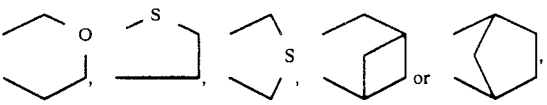

its optical antipode or pharmaceutically acceptable acid addition salt thereof, and a memory enhancing agent containing these compounds as an active ingredient.

DESCRIPTION OF THE PREFERRED EMBODIMENTS

The present invention will be described in more detail below.

The 9-acylamino-tetrahydroacridine derivatives of the present invention are represented by the above formula (I).

In the formula (I), R represents an alkyl group such as an alkyl group having 2 to 8 carbon atoms, preferably an alkyl group having 2 to 4 carbon atoms such as an ethyl group, a n-propyl group, an isopropyl group, a n-butyl group, a sec-butyl group and a tert-butyl group; an aralkyl group such as

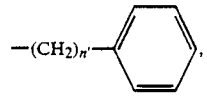

n′ = 1 to 3; or a group represented by the above formula (II).

In the formula (II), an alkyl group represented by $R^1$ and $R^3$ may include an alkyl group having 1 to 6 carbon atoms, preferably an alkyl group having 1 to 4 carbon atoms such as a methyl group, an ethyl group, a n-propyl group, an isopropyl group, a n-butyl group and a sec-butyl group.

Also, in the formula (I), a halogen atom, an alkyl group, an alkoxy group or an aralkyl group represented by $R^4$ to $R^7$ may be mentioned as follows. The halogen atom may include a fluorine atom, a chlorine atom, a bromine atom or an iodine atom; the alkyl group may include an alkyl group having 1 to 4 carbon atoms such as a methyl group, an ethyl group, a n-propyl group, an isopropyl group, a n-butyl group, a sec-butyl group, etc.; the alkoxy group may include an alkoxy group having 1 to 4 carbon atoms such as a methoxy group, an ethoxy group, a n-propoxy group, an isopropoxy group, a n-butoxy group, a sec-butoxy group, etc.; and the aralkyl group may include a benzyl group, a phenethyl group, etc.

Of the compounds represented by the formula (I), examples of the preferred substituents for the compound may include as follows:

(1) As the R, a n-propyl group, an isopropyl group or the compound represented by the formula (II). Particularly preferred are the compound wherein R is the group of the formula (II) and

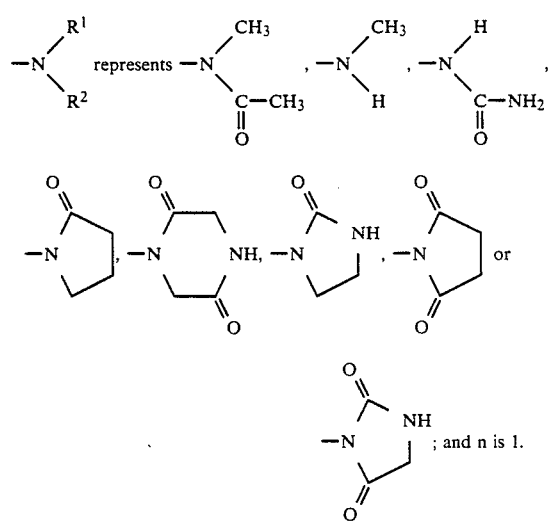

$-N\begin{smallmatrix}R^1\\R^2\end{smallmatrix}$ represents $-N\begin{smallmatrix}CH_3\\C-CH_3\\\|\\O\end{smallmatrix}$, $-N\begin{smallmatrix}CH_3\\H\end{smallmatrix}$, $-N\begin{smallmatrix}H\\C-NH_2\\\|\\O\end{smallmatrix}$, (pyrrolidinone), (piperazinedione-NH), (imidazolidinone-NH), (succinimide) or (hydantoin-NH); and n is 1.

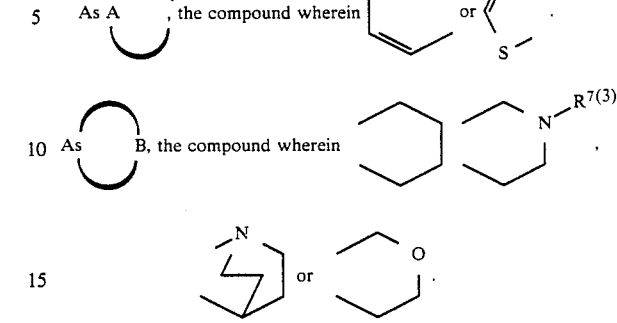

As A, the compound wherein (benzene) or (thiophene) . (2)

As B, the compound wherein (piperidine-$NR^{7}$) (3)

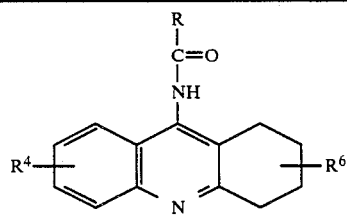

or (pyran).

Specific examples of the compound of the present invention will be described in Table 1 and Table 2.

TABLE 1

$$\text{(I)}$$

Structure: 9-acylamino-1,2,3,4-tetrahydroacridine with substituents $R^4$ and $R^6$, acyl group $R-C(=O)-NH-$

| Compound No. | R | n | $R^1$ | $R^2$ | $R^4$ | $R^6$ |
|---|---|---|---|---|---|---|
| 1 | $-C_2H_5$ | — | — | — | H | H |
| 2 | $-C_3H_7$ | — | — | — | H | H |
| 3 | $-CH(CH_3)_2$ | — | — | — | H | H |
| 4 | $-C_4H_9$ | — | — | — | H | H |
| 5 | $-CH_2-CH(CH_3)_2$ | — | — | — | H | H |
| 6 | $-CH(CH_3)-C_2H_5$ | — | — | — | H | H |
| 7 | $-CH_2-C_6H_5$ | — | — | — | H | H |
| 8 | $-C_3H_7$ | — | — | — | H | 2-OH |
| 9 | $-C_3H_6-C_6H_5$ | — | — | — | H | H |
| 10 | $-(CH_2)_n-NR^1R^2$ | 1 | H | H | H | H |

TABLE 1-continued $$\text{(I)}$$

[Structure: 9-acylamino-1,2,3,4-tetrahydroacridine with R-C(=O)-NH- at position 9, R⁴ on benzene ring, R⁶ on cyclohexene ring]

| Compound No. | R | n | R¹ | R² | R⁴ | R⁶ |
|---|---|---|---|---|---|---|
| 11 | $-(CH_2)_n-N(R^1)(R^2)$ | 1 | H | $-CH_3$ | H | H |
| 12 | $-(CH_2)_n-N(R^1)(R^2)$ | 1 | H | $-C_2H_5$ | H | H |
| 13 | $-(CH_2)_n-N(R^1)(R^2)$ | 1 | H | $-C_3H_7$ | H | H |
| 14 | $-(CH_2)_n-N(R^1)(R^2)$ | 1 | H | $-CH(CH_3)_2$ | H | H |
| 15 | $-(CH_2)_n-N(R^1)(R^2)$ | 2 | H | H | H | H |
| 16 | $-(CH_2)_n-N(R^1)(R^2)$ | 2 | H | $-CH_3$ | H | H |
| 17 | $-(CH_2)_n-N(R^1)(R^2)$ | 1 | H | $-C(=O)-CH_3$ | H | H |
| 18 | $-(CH_2)_n-N(R^1)(R^2)$ | 1 | H | $-C(=O)-CH_2-N(\text{2-pyrrolidinon-1-yl})$ | H | H |
| 19 | $-(CH_2)_n-N(R^1)(R^2)$ | 1 | $-CH_3$ | $-C(=O)-CH_3$ | H | H |
| 20 | $-(CH_2)_n-N(R^1)(R^2)$ | 1 | H | $-C(=O)-NH_2$ | H | H |
| 21 | $-(CH_2)_n-N(R^1)(R^2)$ | 1 | H | $-C(=O)-NH-CH_3$ | H | H |

TABLE 1-continued $$\text{(I)}$$

Structure: 9-position NH-C(=O)-R substituted 1,2,3,4-tetrahydroacridine with $R^4$ and $R^6$ substituents.

| Compound No. | R | n | $R^1$ | $R^2$ | $R^4$ | $R^6$ |
|---|---|---|---|---|---|---|
| 22 | $-(CH_2)_n-N(R^1)(R^2)$ | 2 | H | $-C(=O)-NH_2$ | H | H |
| 23 | $-(CH_2)_n-N(R^1)(R^2)$ | 1 | H | $-CH_2-C(=O)-OH$ | H | H |
| 24 | $-(CH_2)_n-N(R^1)(R^2)$ | 1 | H | $-CH_2-C(=O)-OC_2H_5$ | H | H |
| 25 | $-(CH_2)_n-N(R^1)(R^2)$ | 2 | H | $-CH_2-C(=O)-OC_2H_5$ | H | H |
| 26 | $-(CH_2)_n-N(R^1)(R^2)$ | 1 | combinedly 2-oxopyrrolidin-1-yl | | H | H |
| 27 | $-(CH_2)_n-N(R^1)(R^2)$ | 2 | combinedly 2-oxopyrrolidin-1-yl | | H | H |
| 28 | $-(CH_2)_n-N(R^1)(R^2)$ | 1 | combinedly 2,6-dioxopiperazin-1-yl | | H | H |
| 29 | $-(CH_2)_n-N(R^1)(R^2)$ | 2 | combinedly 2,6-dioxopiperazin-1-yl | | H | H |
| 30 | $-(CH_2)_n-N(R^1)(R^2)$ | 1 | combinedly succinimido (2,5-dioxopyrrolidin-1-yl) | | H | H |

TABLE 1-continued (I) Structure: R-C(=O)-NH- attached to tetrahydroacridine with R⁴ on benzene ring and R⁶ on cyclohexane ring.

| Compound No. | R | n | R¹ | R² | R⁴ | R⁶ |
|---|---|---|---|---|---|---|
| 31 | —(CH₂)ₙ—N(R¹)(R²) | 2 | combinedly | succinimide (—N in 5-ring with two C=O) | H | H |
| 32 | —(CH₂)ₙ—N(R¹)(R²) | 1 | combinedly | 2-oxoimidazolidine (—N, C=O, NH in 5-ring) | H | H |
| 33 | —(CH₂)ₙ—N(R¹)(R²) | 2 | combinedly | 2-oxoimidazolidine (—N, C=O, NH in 5-ring) | H | H |
| 34 | —(CH₂)ₙ—N(R¹)(R²) | 1 | combinedly | 2-oxopiperidine (—N, C=O in 6-ring) | H | H |
| 35 | —(CH₂)ₙ—N(R¹)(R²) | 1 | combinedly | glutarimide (—N in 6-ring with two C=O) | H | H |
| 36 | —(CH₂)ₙ—N(R¹)(R²) | 1 | combinedly | 2-oxohexahydropyrimidine (—N, C=O, NH in 6-ring) | H | H |
| 37 | —(CH₂)ₙ—N(R¹)(R²) | 1 | combinedly | 2,5-dioxopiperazine (—N, C=O, NH, C=O in 6-ring) | H | H |
| 38 | —(CH₂)ₙ—N(R¹)(R²) | 2 | combinedly | 2,5-dioxopiperazine (—N, C=O, NH, C=O in 6-ring) | H | H |
| 39 | —(CH₂)ₙ—N(R¹)(R²) | 1 | combinedly | imidazole (—N, N in 5-ring) | H | H |

TABLE 1-continued
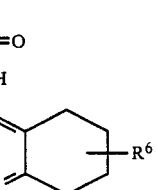
(I)
| Compound No. | R | n | R¹ | R² | R⁴ | R⁶ |
|---|---|---|---|---|---|---|
| 40 | −(CH₂)ₙ−N(R¹)(R²) | 2 | combinedly | 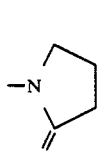 | H | H |
| 41 | −(CH₂)ₙ−N(R¹)(R²) | 1 | combinedly | 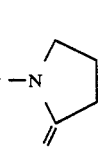 | 7-CH₃ | H |
| 42 | −(CH₂)ₙ−N(R¹)(R²) | 1 | combinedly | 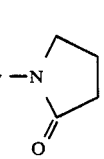 | 5-CH₃ | H |
| 43 | −(CH₂)ₙ−N(R¹)(R²) | 1 | combinedly | 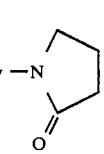 | 7-Br | H |
| 44 | −(CH₂)ₙ−N(R¹)(R²) | 1 | combinedly | 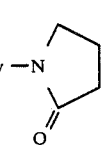 | 7-Cl | H |
| 45 | −(CH₂)ₙ−N(R¹)(R²) | 1 | combinedly | 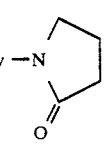 | 8-F | H |
| 46 | −(CH₂)ₙ−N(R¹)(R²) | 1 | combinedly | 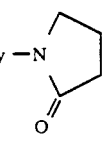 | 6-OCH₃ | H |
| 47 | −(CH₂)ₙ−N(R¹)(R²) | 1 | combinedly | 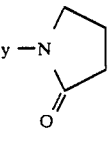 | 7-OC₂H₅ | H |
| 48 | −(CH₂)ₙ−N(R¹)(R²) | 1 | combinedly | | 6-OH | H |

TABLE 1-continued (I)

| Compound No. | R | n | R¹ | R² | R⁴ | R⁶ |
|---|---|---|---|---|---|---|
| 49 | $-(CH_2)_n-N\begin{smallmatrix}R^1\\R^2\end{smallmatrix}$ | 1 | | combinedly pyrrolidin-2-one | H | 2-CH₃ |
| 50 | $-(CH_2)_n-N\begin{smallmatrix}R^1\\R^2\end{smallmatrix}$ | 1 | | combinedly pyrrolidin-2-one | H | 2-C₂H₅ |
| 51 | $-(CH_2)_n-N\begin{smallmatrix}R^1\\R^2\end{smallmatrix}$ | 1 | | combinedly pyrrolidin-2-one | H | 4-CH₃ |
| 52 | $-(CH_2)_n-N\begin{smallmatrix}R^1\\R^2\end{smallmatrix}$ | 1 | | combinedly pyrrolidin-2-one | H | 4-C₂H₅ |
| 53 | $-(CH_2)_n-N\begin{smallmatrix}R^1\\R^2\end{smallmatrix}$ | 1 | | combinedly pyrrolidin-2-one | H | 1-OH |
| 54 | $-(CH_2)_n-N\begin{smallmatrix}R^1\\R^2\end{smallmatrix}$ | 1 | | combinedly pyrrolidin-2-one | H | 2-OH |
| 55 | $-(CH_2)_n-N\begin{smallmatrix}R^1\\R^2\end{smallmatrix}$ | 1 | | combinedly pyrrolidin-2-one | 7-CH₃ | 2-CH₃ |
| 56 | $-(CH_2)_n-N\begin{smallmatrix}R^1\\R^2\end{smallmatrix}$ | 1 | | combinedly pyrrolidin-2-one | 7-Cl | 4-CH₃ |
| 57 | $-(CH_2)_n-N\begin{smallmatrix}R^1\\R^2\end{smallmatrix}$ | 1 | | combinedly pyrrolidin-2-one | 8-F | 1-OH |

TABLE 1-continued $$\text{(I)}$$

| Compound No. | R | n | R$^1$ | R$^2$ | R$^4$ | R$^6$ |
|---|---|---|---|---|---|---|
| 58 | —(CH$_2$)$_n$—N(R$^1$)(R$^2$) | 1 | combinedly | 2-pyrrolidinon-1-yl | 8-F | 2-OH |
| 59 | —(CH$_2$)$_n$—N(R$^1$)(R$^2$) | 1 | combinedly | 2-pyrrolidinon-1-yl | 6-OCH$_3$ | 1-OH |
| 60 | —(CH$_2$)$_n$—N(R$^1$)(R$^2$) | 1 | combinedly | 2-pyrrolidinon-1-yl | 6-OH | 2-CH$_3$ |
| 61 | —(CH$_2$)$_n$—N(R$^1$)(R$^2$) | 1 | combinedly | 2,6-dioxopiperazin-1-yl | 8-F | H |
| 62 | —(CH$_2$)$_n$—N(R$^1$)(R$^2$) | 1 | combinedly | 2,6-dioxopiperazin-1-yl | H | 1-CH$_3$ |
| 63 | —(CH$_2$)$_n$—N(R$^1$)(R$^2$) | 1 | combinedly | 2,6-dioxopiperazin-1-yl | H | 2-OH |
| 64 | —(CH$_2$)$_n$—N(R$^1$)(R$^2$) | 1 | combinedly | 2,6-dioxopiperazin-1-yl | 7-OC$_2$H$_5$ | H |

TABLE 1-continued

| Compound No. | R | n | R¹ | R² | R⁴ | R⁶ |
|---|---|---|---|---|---|---|
| 65 | $-(CH_2)_n-N\begin{smallmatrix}R^1\\R^2\end{smallmatrix}$ | 1 | combinedly | 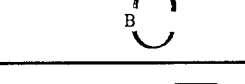 | 7-Cl | 2-OH |

TABLE 2

| Compound No. | R | n | R¹ | R² | A | B |
|---|---|---|---|---|---|---|
| 66 | $-(CH_2)_n-N\begin{smallmatrix}R^1\\R^2\end{smallmatrix}$ | 1 | combinedly | 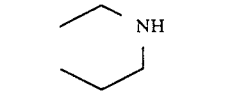 | benzene ring |  |
| 67 | $-(CH_2)_n-N\begin{smallmatrix}R^1\\R^2\end{smallmatrix}$ | 1 | combinedly | 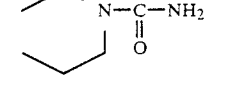 | benzene ring | NH |
| 68 | $-(CH_2)_n-N\begin{smallmatrix}R^1\\R^2\end{smallmatrix}$ | 1 | combinedly |  | benzene ring | 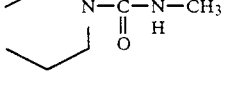 |
| 69 | $-(CH_2)_n-N\begin{smallmatrix}R^1\\R^2\end{smallmatrix}$ | 1 | combinedly |  | benzene ring | N—C—N—CH₃ ‖ H O |
| 70 | $-(CH_2)_n-N\begin{smallmatrix}R^1\\R^2\end{smallmatrix}$ | 1 | combinedly | 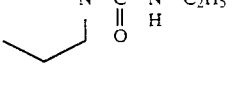 | benzene ring | N—C—N—C₂H₅ ‖ H O |

TABLE 2-continued (I)

| Compound No. | R | n | R¹ | R² | A | B |
|---|---|---|---|---|---|---|
| 71 | $-(CH_2)_n-N\begin{smallmatrix}R^1\\R^2\end{smallmatrix}$ | 1 | combinedly | pyrrolidin-2-on-1-yl | benzene | piperidin-N-formyl |
| 72 | $-(CH_2)_n-N\begin{smallmatrix}R^1\\R^2\end{smallmatrix}$ | 1 | combinedly | pyrrolidin-2-on-1-yl | benzene | N-methylpiperidine |
| 73 | $-(CH_2)_n-N\begin{smallmatrix}R^1\\R^2\end{smallmatrix}$ | 1 | combinedly | 2,5-dioxopiperazin-1-yl | benzene | N-methylpiperidine |
| 74 | $-C_3H_7$ | — | — | | benzene | cyclohexane |
| 75 | $-(CH_2)_n-N\begin{smallmatrix}R^1\\R^2\end{smallmatrix}$ | 1 | combinedly | pyrrolidin-2-on-1-yl | benzene | cyclohexane |
| 76 | $-C_3H_7$ | — | — | | benzene | cyclohexanone |
| 77 | $-(CH_2)_n-N\begin{smallmatrix}R^1\\R^2\end{smallmatrix}$ | 1 | combinedly | pyrrolidin-2-on-1-yl | benzene | cyclohexanone |
| 78 | $-C_3H_7$ | — | — | | benzene | pyridine-like |
| 79 | $-(CH_2)_n-N\begin{smallmatrix}R^1\\R^2\end{smallmatrix}$ | 1 | combinedly | pyrrolidin-2-on-1-yl | benzene | pyridine-like |

TABLE 2-continued
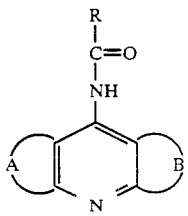
(I)
| Compound No. | R | n | R¹ | R² | A | B |
|---|---|---|---|---|---|---|
| 80 | −(CH₂)ₙ−N(R¹)(R²) | 1 | combinedly | 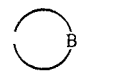 | 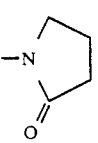 |  |
| 81 | −(CH₂)ₙ−N(R¹)(R²) | 1 | combinedly |  | 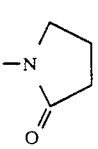 | 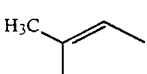 |
| 82 | −(CH₂)ₙ−N(R¹)(R²) | 1 | combinedly | 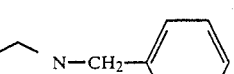 | 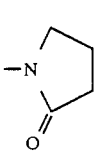 | 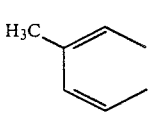 |
| 83 | −(CH₂)ₙ−N(R¹)(R²) | 1 | combinedly | 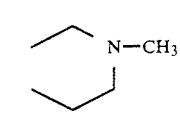 | 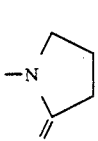 | 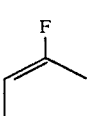 |
| 84 | −(CH₂)ₙ−N(R¹)(R²) | 1 | combinedly | 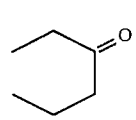 | 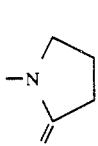 | 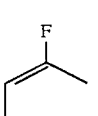 |
| 85 | −(CH₂)ₙ−N(R¹)(R²) | 1 | combinedly | 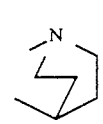 | 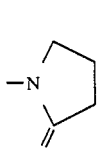 | 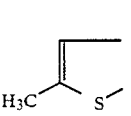 |
| 86 | −(CH₂)ₙ−N(R¹)(R²) | 1 | combinedly | 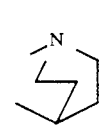 | 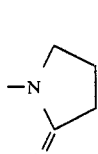 |  |
| 87 | −(CH₂)ₙ−N(R¹)(R²) | 1 | combinedly |  | 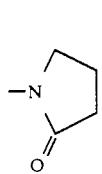 |  |

TABLE 2-continued
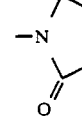
(I)
| Compound No. | R | n | R¹ | R² | A | B |
|---|---|---|---|---|---|---|
| 88 | $-(CH_2)_n-N{<}^{R^1}_{R^2}$ | 1 | combinedly | 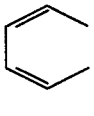 | 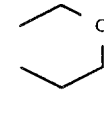 | 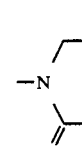 |
| 89 | $-(CH_2)_n-N{<}^{R^1}_{R^2}$ | 1 | combinedly | 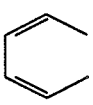 | 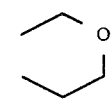 | 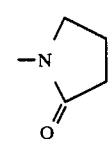 |
| 90 | $-(CH_2)_n-N{<}^{R^1}_{R^2}$ | 1 | combinedly | 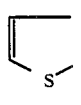 | 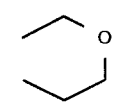 | 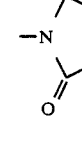 |
| 91 | $-(CH_2)_n-N{<}^{R^1}_{R^2}$ | 1 | combinedly | 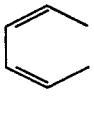 | 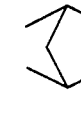 | 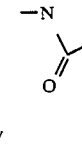 |
| 92 | $-(CH_2)_n-N{<}^{R^1}_{R^2}$ | 1 | combinedly | 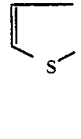 | 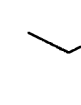 | 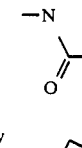 |
| 93 | $-(CH_2)_n-N{<}^{R^1}_{R^2}$ | 1 | combinedly |  | 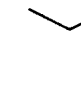 | 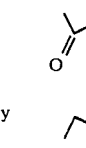 |
| 94 | $-(CH_2)_n-N{<}^{R^1}_{R^2}$ | 1 | combinedly | 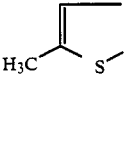 | 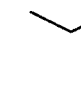 |  |
| 95 | $-(CH_2)_n-N{<}^{R^1}_{R^2}$ | 1 | combinedly |  |  | |

TABLE 2-continued

| Compound No. | R | n | R¹ | R² | A | B |
|---|---|---|---|---|---|---|
| 96 | —(CH₂)ₙ—N(R¹)(R²) | 1 | combinedly | pyrrolidinone-N— | benzene ring | thiolane ring |
| 97 | —(CH₂)ₙ—N(R¹)(R²) | 1 | combinedly | pyrrolidinone-N— | benzene ring | cyclobutane ring |

Particularly preferred compounds of the present invention may include the compounds Nos. 2, 3, 11, 19, 20, 23, 26, 28, 30, 32, 34, 37, 39, 41, 44, 45, 54, 61, 63, 64, 66 to 69, 72, 73, 77 to 80, 83, 84, 88, 89 and 92 to 94 in the above Table 1 and Table 2.

As the salts of the compounds represented by the formula (I), physiologically acceptable salts are preferred, and they may include an inorganic acid salt such as hydrochlorides, hydrobromides, hydroiodides, sulfates, phosphates, etc.; and an organic acid salt such as oxalates, maleates, fumarates, lactates, malates, citrates, tartarates, benzoates, methansulfonates, etc. Since the compounds of the formula (I) or salts thereof may be present in the form of hydrates or solvates, the hydrates and solvates thereof are also included in the compounds of the present invention.

Next, the process for preparing the compounds of the present invention will be described.

The compounds of the present invention can be prepared by, for example, any of the following methods.

(1) By reacting the compound represented by the formula (III):

wherein

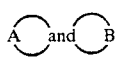

have the same meanings as defined in the above formula (I),
with a reactive derivative of the compound represented by the formula (IV):

$$R^{10}-\underset{\underset{O}{\|}}{C}-OH \qquad (IV)$$

wherein $R^{10}$ represents an alkyl group or an aralkyl group which are represented by R in the formula (I),
the compound represented by the formula (I) can be obtained.

Examples of the reactive derivatives of the compound of the formula (IV) are preferably symmetric acid anhydrides or acid halides (particularly acid chloride). The reaction is carried out in the presence of an inert solvent such as benzene, toluene, xylene, 1,2-dichloroethane, 1,1,2,2-tetrachloroethane, etc., or by using excessive amounts of symmetric acid anhydrides or acid halides as a solvent. When the symmetric acid anhydrides are used, a tertiary amine such as pyridine may be used. The reaction is carried out at the temperature in the range of 30° to 150° C., preferably 50° to 120° C.

(2) After processing the compound represented by the above formula (III) with an equimolar amount or more of sodium hydride to prepare a sodium salt, reacting it with an ester compound represented by the formula (V):

$$R^{11}-\underset{\underset{O}{\|}}{C}-O-R^{12} \qquad (V)$$

wherein $R^{11}$ represents

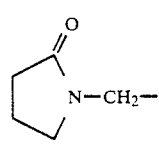

or

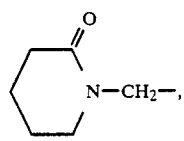

and $R^{12}$ represents a methyl group or an ethyl group, to obtain the compound represented by the formula (1).

As the solvent, preferred are tetrahydrofuran, dioxane, acetonitrile, dimethylformamide, N-methylpyrrolidone, dimethylsulfoxide, etc. The reaction is carried out at the temperature in the range of 10° to 80° C., preferably 30° to 60° C.

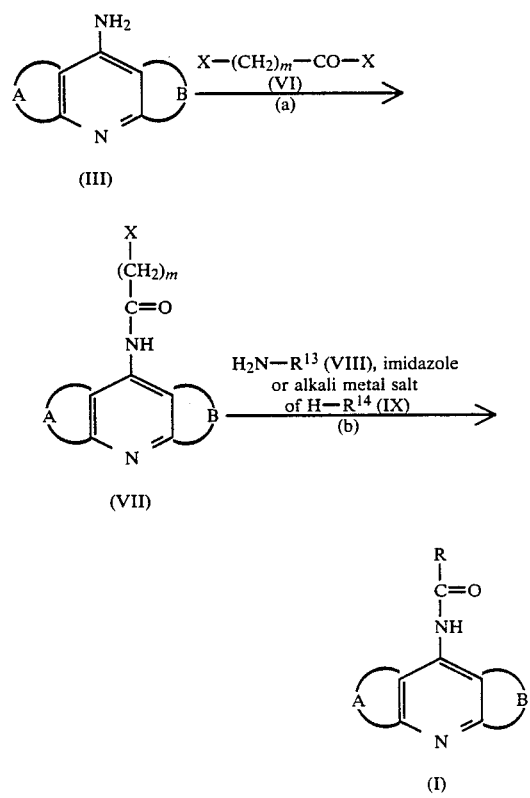

wherein X represents a chlorine atom or a bromine atom; m represents 1 or 2;

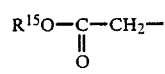

have the same meanings as defined in the formula (I); $R^{13}$ in the formula (VIII) represents a straight or branched alkyl group having 1 to 4 carbon atoms; or $$R^{15}O-\underset{\underset{O}{\|}}{C}-CH_2-$$

($R^{15}$ represents an alkyl group having 1 to 4 carbon atoms); in the formula (IX) represents

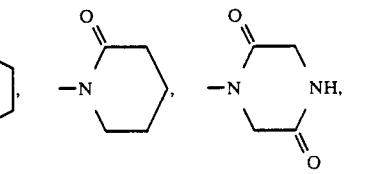

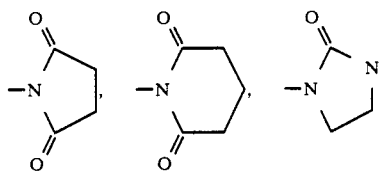

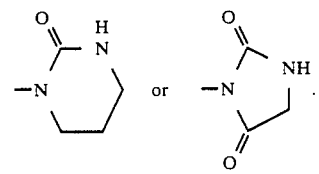

By the above two steps of the reaction formulae, the compound of the formula (I) can be synthesized.

That is, an acyl halide compound of the formula (VI) is reacted with the compound of the formula (III) to obtain the compound of the formula (VII) [step (a)]. Then, to the compound of the formula (VII), the compound of the formula (VIII) or imidazole is reacted, or else a compound which is a sodium salt obtained by treating the compound of the formula (IX) with sodium hydride [step (b)], the corresponding compound (I) can be obtained.

The step (a) is carried out by using an excessive amount of acyl halide also as the solvent, or by using an inert solvent such as benzene, toluene, xylene, 1,2-dichloroethane, 1,1,2,2-tetrachloroethane, etc, at the temperature in the range of 50° to 150° C., preferably 70° to 120° C.

The step (b) is carried out by using an excessive amount of amine also as the solvent, or by using an alcoholic solvent such as methanol, ethanol, n-propanol, isopropanol, n-butanol, etc., or a solvent such as tetrahydrofuran, dioxane, acetonitrile, dimethylformamide, dimethylsulfoxide, etc., at the temperature in the range of 0° to 150° C., preferably 20° to 100° C. When the sodium salt of the compound of the formula (IX) is reacted, the reaction is carried out by using a solvent such as tetrahydrofuran, dioxane, acetonitrile, dimethylformamide, dimethylsulfoxide, etc., at the temperature in the range of 0° to 120° C., preferably 20° to 80° C.

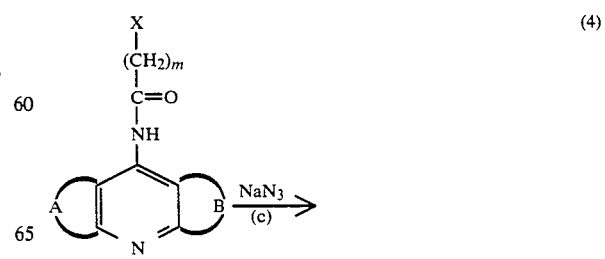

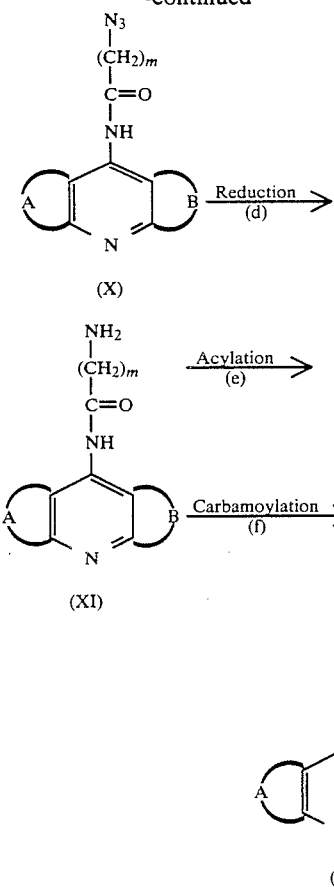

wherein X, m,

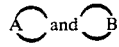

have the same meanings as defined above.

By using the above compound of the formula (VII), the compound of the formula (I) can be obtained through the above three steps reactions.

That is, sodium azide is reacted with the compound of the formula (VII) [step (c)] to obtain the azide compound of the formula (X), the compound is reduced [step (d)] with the method of hydrogenolysis by using, for example, palladium as a catalyst to obtain a primary amine compound of the formula (XI), and then the compound is subjected to acylation [step (e)] or carbamoylation [step (f)] to obtain the compound of the formula (I).

The step (c) is carried out in a solvent such as dimethylformamide, dimethylsulfoxide, acetonitrile, methanol, ethanol, n-propanol, isopropanol, etc., or in a mixed solvent of the above solvents and water at the temperature in the range of 0° to 80°° C., preferably 10° to 50° C.

The steps (d) is carried out in a solvent such as methanol, ethanol, n-propanol, isopropanol, tetrahydrofuran, dioxane, acetonitrile, etc. at the temperature in the range of 0° to 80° C., preferably 10° to 40° C.

The steps (e) is carried out under the usual acylation conditions, for example, in the presence of a tertiary amine, by reacting with an acyl halide compound or a symmetrical acid anhydride.

The step (f) may be carried out under the conditions of the usual carbamoylation conditions. For example, when the compound of the formula (XI) is reacted with alkylisocyanate, an alkyl-substituted urea can be obtain and when it is reacted with sodium isocyanate in acetic acid, a a urea derivative can be obtained.

(5) As a method for converting one compound of the formula (I) into the other compound included in the formula (I), the following methods are present.

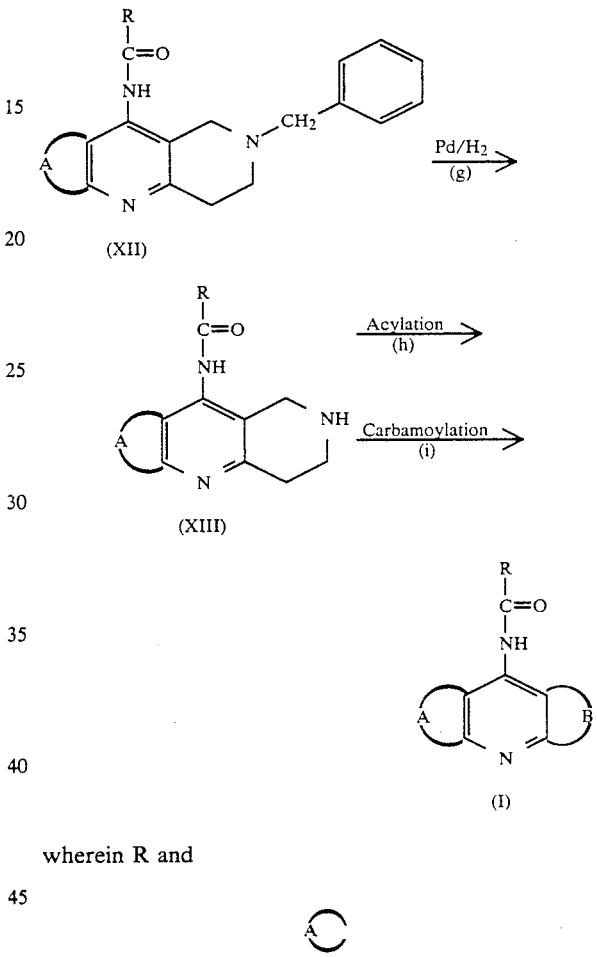

wherein R and

A in the formulae (XII) and (XIII) have the same meanings as defined in the above formula (I).

That is, N-benzylamine represented by the formula (XII) is subjected to debenzylation by hydrogenolysis using palladium as the catalyst [step (g)], and then the obtained secondary amine of the formula (XIII) is subjected to acylation [step (h)] or carbamoylation [step (i)].

The step (g) can be carried out by the usual method, for example, hydrogenolysis is conducted by using palladiumcarbon as the catalyst and by adding hydrochloric acid. The steps (h) and (i) can be carried out by the same methods of the above steps (e) and (f) in the above item (4), respectively.

The compound of the formula (III) which is the starting material of the preparative methods of the above (1) to (3) can be easily synthesized by the method, for example, as described in (a) Tetrahedron Letters, p. 1277 (1963); (b) Collection of Czechoslovak Chemical Communications, Vol. 42, p. 2802 (1977); (c) Acta Chemica Scandinavica, B, Vol. 33, p. 313 (1979); etc. or corresponding methods thereto.

Also, it may be synthesized in the manner as disclosed in each publication of Japanese Provisional Patent Publications No. 148154/1986, No. 141980/1988, No. 166881/1988, No. 203664/1988, No. 225358/1988, No. 238063/1988 and No. 239271/1988; and EP-A-268,871.

When the compound of the present invention is used as a therapeutic agent, it may be administered singly or as a composite by compounding with a carrier which is pharmaceutically acceptable. Compositions thereof may be determined by the solubility, chemical properties, route of administration, administration scheme, etc. of the compounds.

For example, it may be administered orally in the form of granules, fine grains, powders, tablets, hard capsules, soft capsules, syrups, emulsions, suspensions or liquids, or may be administered intravenously, intramuscularly or hypodermically as an injection.

Also, by making a powder for injection, it may be used by preparing when using it. An organic or inorganic carrier which is in the form of solid or liquid, or a diluent, which are pharmaceutically acceptable for oral, rectal, parenteral or local administration may be used in combination with the compound of the present invention. As excipients to be used for preparing solid preparations, for example, lactose, sucrose, starch, talc, cellulose, dextrin, kaolin, calcium carbonate, etc. are used. Liquid preparations for oral administration, that is, emulsions, syrups, suspensions, liquids, etc. contain inert diluents which are conventionally used such as water or a vegetable oils, etc. This preparation may be contained, in addition to the inert diluents, such as auxiliaries, e.g. wettables, suspension auxiliaries, sweeteners, aromatics, colorants or preservatives, etc. It may be made in the form of liquid preparations and contained in a capsule made of a substance which is absorbable such as gelatin, etc. As the preparations for parenteral administration, that is, solvents or suspending agents to be used for preparation of injections, etc., there may be mentioned, for example, water, propylene glycol, polyethylene glycol, benzyl alcohol, ethyl oleate, lecithin, etc. Preparative methods of the preparations may be based on the conventional method.

Regarding a clinical dosage, when it is used via oral administration, a dose per day is generally 1 to 1000 mg, preferably 1 to 100 mg of the compound of the present invention per an adult, but the dose may be optionally varied depending upon age, severity of disease, condition of the patient, presence or absence of simultaneous administration, etc. The above dose per day of the compound of the present invention may be administered once per day or may be administered twice or three times per day with suitable intervals by dividing it, or may be administered intermittently.

Also, when it is used as injections, it is used as the dose per day of 0.1 to 100 mg, preferably 0.1 to 50 mg as the compound of the present invention per an adult.

While the compound of the present invention represented by the formula (I) thus prepared is weak in acetylcholine esterase inhibiting ability as 1/100 or less as compared with the known 9-amino-tetrahydroacridine, neurotransmission can be heightened by activating a presynaptic site of the cholinergic neurons. More specifically, high affinity-choline uptake in hippocampus synaptosome of rat injected AF64A (ethylcholine aziridinium ion) [Journal of Pharmacology and Experimental Therapeutics, Vol. 222, p. 140 (1982); Neuropharmacology, Vol. 26, p. 361 (1987)] in cerebral ventricles can be improved (see Test Example 1). This activation could not be found out in 9-amino-tetrahydroacridine.

Also, the compound of the present invention is extremely weak in toxicity and little in adverse reaction as compared with 9-amino-tetrahydroacridine, whereby it can be available therapeutic agent against memory disorder such as Alzheimer's disease, etc.

The compound represented by the formula (I) of the present invention is a physiologically active and valuable compound. Particularly, these compounds have a function of directly activating a decreased cholinergic nervous system so that they are available as pharmaceuticals which are usable for therapy of memory disorder such as Alzheimer's disease.

In senile dimentia, particularly in Alzheimer's disease, functions of cholinergic neurons in brain are decreased, and between this decrease and a degree of memory disorder, good correlation is present. On the other hand, AF64A impairs cholinergic neurons selectively and for the long run as reported by Fisher [Journal of Pharmacology and Experimental Therapeutics, Vol. 222, p. 140 (1982)]and Leventer [Neuropharmacology, Vol. 26, p. 361 (1987)]. In the rat injected with AF64A, defects of memory and study can be admitted [Brain Research, Vol. 321, p. 91 (1984)], so that it is good model for Alzheimer's disease. Accordingly, the compounds of the present invention which can directly activate the function of cholinergic neurons in brain which is decreased by injection of AF64A, can be considered to be available for therapy of senile dimentia including Alzheimer's disease.

EXAMPLES

In the following, the present invention will be described in more detail, but the present invention is not limited by the following Example so long as it does not exceed the summary of the invention.

EXAMPLE 1

Synthesis of
N-(1,2,3,4-tetrahydroacridin-9-yl)butanamide
(Compound No. 2 in Table 1)

In 4 ml of pyridine was added 2 g of 9-amino-1,2,3,4-tetrahydroacridine. To the mixture was added 3.3 ml of n-butyric acid anhydride and the mixture was refluxed for 8 hours. Then, the solvent was removed under reduced pressure, and 10 ml of methanol was added to the obtained residue. Conc. aqueous ammonia was added to the mixture and the mixture was refluxed for one hour. After removal of the solvent under reduced pressure, water was added to the residue and the mixture was extracted with chloroform. The chloroform layer was dried over anhydrous sodium sulfate, and the solvent was removed under reduced pressure. The obtained residue was purified through silica gel column chromatography and recrystallized from chloroform/ether to give 1.57 g of N-(1,2,3,4-tetrahydroacridin-9-yl)butanamide. Melting point: 202° to 204° C.

In the same manner as in Example 1, the compounds shown in Table 3 were synthesized.

REFERENCE EXAMPLE 1

In the same manner as in Example 1, the compound of Reference example 1 was synthesized as shown in Table 3.

TABLE 3
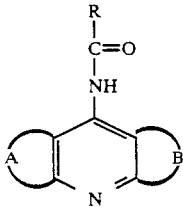
| Example No. | R | | Melting point (°C.) |
|---|---|---|---|
| 2 | —C$_2$H$_5$ | 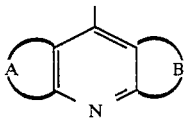 | 228 to 230 |
| 3 | —CH(CH$_3$)$_2$ | 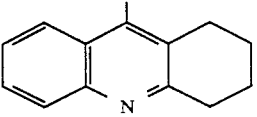 | 245 to 247 |
| 4 | —C$_4$H$_9$ | 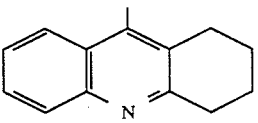 | 242 to 244 (hydrochloride) |
| 5 | —CH$_2$—CH(CH$_3$)$_2$ | 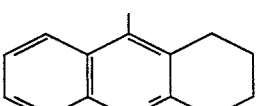 | 241 to 243 |
| 6 | —C$_5$H$_{11}$ | 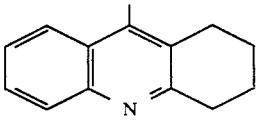 | 201 to 203 (hydrochloride) |
| 7 | —CH$_2$—C$_6$H$_5$ | 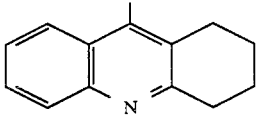 | 223 to 227 (decomposed) |
| 8 | —(CH$_2$)$_3$—C$_6$H$_5$ | 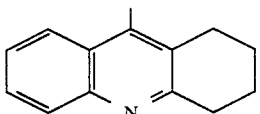 | 141 to 143 |
| 9 | —C$_3$H$_7$ | 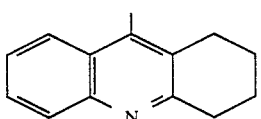 | 208 to 210 |
| 10 | —C$_3$H$_7$ | 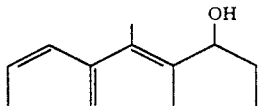 | 171 to 176 (dihydrochloride) |

TABLE 3-continued

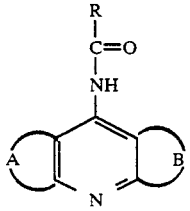

| Example No. | R | | Melting point (°C.) |
|---|---|---|---|
| 11 | —C₃H₇ | 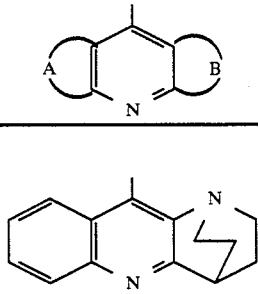 | 177 to 179 |
| 12 | —C₃H₇ | 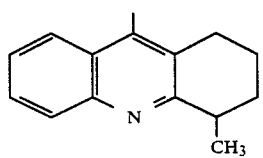 | 180 to 184 |
| 13 | —C₃H₇ | 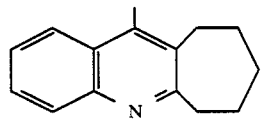 | 190 to 193 |
| Reference example 1 | —C₃H₇ | 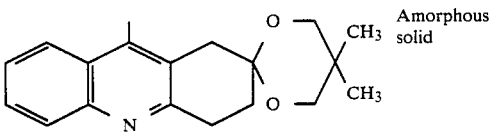 | Amorphous solid |

EXAMPLE 14

Synthesis of 2-(2-oxopyrrolidin-1-yl)-N-(1,2,3,4-tetrahydroacidin-9-yl)acetamide hydrochloride (Compound No. 26 in Table 1)

In 50 ml of N-methylpyrrolidone was suspended 4.4 g (content: 60%) of sodium hydride, and then 10.4 g of 9-amino1,2,3,4-tetrahydroacridine was added to the suspension and the mixture was stirred at room temperature for one hour. Then, the reaction system was elevated to 50° C., and 17.4 g of methyl 2-oxo-1-pyrrolidine acetate was added dropwise to the mixture over 30 minutes. After cooling to 10° C., the mixture was poured into 300 ml of an aqueous solution containing 40 g of ammonium chloride, and extracted with 300 ml of chloroform. The chloroform solution was evaporated to dryness and recrystallized from isopropanol to give 14.9 g of crystal. Melting point: 233° to 236° C. This crystal was suspended in 120 ml of isopropanol, and then 10 ml of 26% hydrogen chloride-isopropanol solution was added thereto. After stirring the mixture at room temperature for one hour, it was filtered to give 15.2 g of the title compound. Melting point: 230° to 235° C. (decomposed).

In the same manner as in Example 14, the compounds shown in the following Table 4 were synthesized.

TABLE 4
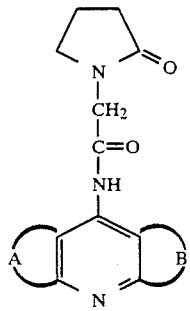
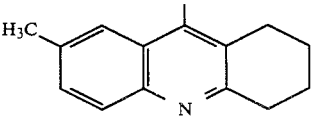
| Example No. | | Melting point (°C.) |
|---|---|---|
| 15 | 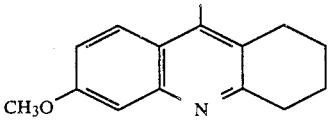 | 216 to 218 |
| 16 | 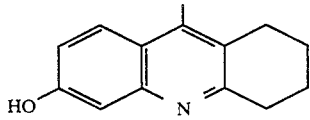 | 230 to 232 |
| 17 | 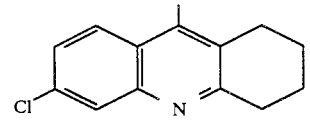 | 288 to 293 |
| 18 | 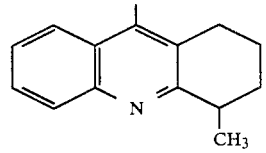 | 229 to 231 |
| 19 | 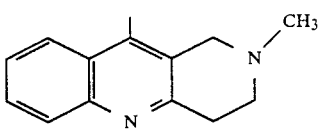 | 174 to 176 |
| 20 | 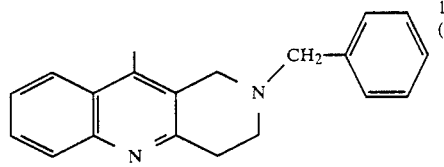 | 169 to 173 (dihydrochloride) |
| 21 |  | 117 to 120 (maleate, 1:1) |

TABLE 4-continued
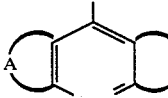
| Example No. | [structure] | Melting point (°C.) |
|---|---|---|
| 22 | 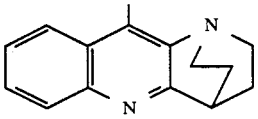 | 143 to 144 |
| 23 | 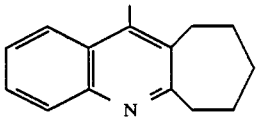 | 203 to 206 |
| 24 | 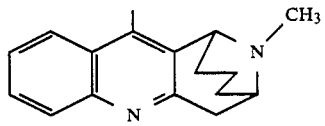 | amorphous solid (maleate, 1:1) |
| 25 | 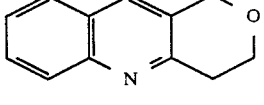 | 199 to 203 |
| 26 | 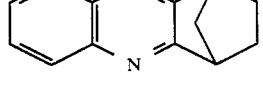 | amorphous solid (maleate, 1:1) |
| 27 | 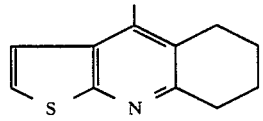 | 199 to 201 |
| 28 | 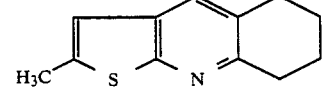 | 212 to 214 |
| 29 | 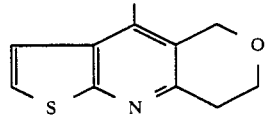 | 200 to 202 |

TABLE 4-continued

| Example No. | Structure | Melting point (°C.) |
|---|---|---|
| 30 | (thieno-pyridine fused bicyclic structure) | 164 to 165 |
| 31 | (dihydrothieno-quinoline structure) | 230 to 233 |
| 32 | (dihydrothieno-quinoline structure) | 204 to 207 |
| 33 | (acridine with bicyclic substituent) | 153 to 154 |

EXAMPLE 34

Synthesis of 2-(2,4-imidazolidinedione-3-yl)-N-(1,2,3,4-tetrahydroacridin-9-yl)acetamide (Compound No. 37 of Table 1)

In 20 ml of dimethylformamide was suspended 0.8 g (content: 60%) of sodium hydride, and then 3 g of 2,4-imidazolidinedione was added to the suspension and the mixture was stirred at room temperature for 30 minutes. Then, 2.75 g of 9-chloroacetylamino-1,2,3,4-tetrahydroacridine (described in "Chem. listy, Vol. 51, p. 1906 (1957)") was added to the mixture and reaction was carried out by heating to 80° C. for 30 minutes. After cooling to 10° C., the mixture was poured into 100 ml of an aqueous solution containing 8 g of ammonium chloride. Precipitated crystals were collected by filtration, washed with water and dried. These crystals were recrystallized from methanol-chloroform to give 2.5 g of the title compound. Melting point: 302° to 304° C. (decomposed).

In the same manner as in Example 34, the compounds shown in the following Table 5 were synthesized.

TABLE 5

| Example No. | ©  | Melting point (°C.) |
|---|---|---|
| 35 | (succinimide group) | 276 to 279 |

TABLE 5-continued

[Structure: 9-(acetylamino)-1,2,3,4-tetrahydroacridine core with CH₂ substituent labeled ©]

| Example No. | © | Melting point (°C.) |
|---|---|---|
| 36 | [pyrrolidinone NH structure] | 247 to 250 |
| 37 | [piperazine-2,5-dione structure] | 260 to 266 (decomposed) |
| 38 | [piperidin-2-one structure] | 233 to 234 |

TABLE 6

[Structure: 9-(acetylamino)-1,2,3,4-tetrahydroacridine core with CH₂ substituent labeled ⓓ]

| Example No. | ⓓ | Melting point (°C.) |
|---|---|---|
| 40 | H\N/CH₂—C—OC₂H₅ (∥O) | 106 to 108 |
| 41 | [pyrazole N-substituent] | 248 to 252 |
| 42 | H₃C\N/C—CH₃ (∥O) | 208 to 210 |

EXAMPLE 39

Synthesis of 9-[(2-methylamino)acetyl-amino]-1,2,3,4-tetrahydroacridine (Compound No. 11 in Table 1)

In 30 ml of a 40% methyl amine-methanol solution was added 1.4 g of 9-chloroacetylamino-1,2,3,4-tetrahydroacridine, and the mixture was reacted at room temperature for 2 hours and then at 50 l° C. for 30 minutes. Then, the mixture was extracted by adding 60 ml of water and 80 ml of chloroform. The chloroform solution was condensed and purified through silica gel column chromatography (chloroform-methanol), and recrystallized from isopropanol-diethyl ether to give 0.89 g of the title compound. Melting point: 152° to 155° C.

In the same manner as in Example 39, the compounds of Examples 40 and 41 were synthesized. Also, the compound of Example 39 was subjected to acetylation with acetic acid anhydride - pyridine in the conventional manner to synthesize the compound of the following Example 42. Melting points of these compounds are shown in Table 6.

EXAMPLE 43

Synthesis of 9-[(2-amino)acetyl-amino]-1,2,3,4-tetrahydroacridine (Compound No. 10 in Table 1)

In 40 ml of dimethylformamide was suspended 2.84 g of sodium azide, and 10 g of 9-chloroacetylamino-1,2,3,4-tetrahydroacridine was added thereto and the mixture was reacted at room temperature for 2 hours. After addition of 32 ml of water to the mixture, precipitated crystals were filtered to give 9.7 g of 9-azidoacetylamino-1,2,3,4-tetrahydroacridine. Melting point: 190° C. (decomposed). These crystals were suspended in 500 ml of methanol, and hydrogenolysis was carried out by adding 0.5 g of palladium black at room temperature for one hour. After removal of the catalyst by filtration, the filtrate was condensed and recrystallized from methanol - isopropanol, and then filtered to give 7.4 g of the title compound. Melting point: 225° to 230° C.

The compound of Example 43 was subjected to acylation or carbamoylation in the conventional manner to synthesize the compounds shown in the following Table 7.

TABLE 7

[Structure: tetrahydroacridine with -NH-C(=O)-CH2-E substituent at 9-position]

| Example No. | E | Melting point (°C.) |
|---|---|---|
| 44 | H, N, C(=O)-CH3 (oxazoline-type) | 242 to 244 |
| 45 | H, N, C(=O)-CH2-N(pyrrolidinone) | 255 to 257 |
| 46 | H, N, C(=O)-NH2 | 248 to 253 (decomposed) |
| 47 | H, N, C(=O)-NH-CH3 | 255 to 258 |

EXAMPLE 48

Synthesis of 2-(2-oxopyrrolidin-1-yl)-N-(1,2,3,4-tetrahydrobenzo[b][1,6]naphthylidin-10-yl)acetamide maleate (1:1) (Compound No. 67 in Table 2)

In a mixed solvent of 200 ml of ethanol and 100 ml of acetic acid was dissolved 10.2 g of free base of the compound of Example 21, and the hydrogenolysis was carried out by adding 6 ml of a 30% hydrogen chloride-ethanol solution and 1.5 g of a 5% palladium-carbon at atmospheric pressure and 50° C. for 6 hours. After removal of the catalyst by filtration, the solvent was evaporated to dryness and the residual solid was recrystallized from ethanol to give 8.7 g of crude crystals. These crystals were added into 100 ml of a saturated sodium hydrogen carbonate aqueous solution and 150 ml of chloroform and the mixture was stirred. After drying the chloroform solution over sodium sulfate, chloroform was removed and the residue was dissolved in 60 ml of methanol. Then, 60 ml methanol solution containing 2.6 g of maleic acid therein was added to the solution and precipitated crystals were collected by filtration to give 7.5 g of the title compound. Melting point: 192° to 198° C. (decomposed).

Free base of the compound of Example 48 was subjected to acylation or carbamoylation in the conventional manner to synthesize the compounds shown in the following Table 8.

TABLE 8

[Structure: benzo-naphthyridine system with -NH-C(=O)-CH2-N(pyrrolidinone) and N-G substituent]

| Example No. | G | Melting point (°C.) |
|---|---|---|
| 49 | -C(=O)-CH3 | 172 to 175 (decomposed) (maleate, 1:1) |
| 50 | -C(=O)-N(H)-CH3 | 220 to 222 (decomposed) |
| 51 | -C(=O)-N(H)-C2H5 | 235 to 238 (decomposed) |

EXAMPLE 52

Synthesis of N-(3,4-dihydroacridine-2(1H)one-9-yl)butanamide (Compound No. 76 in Table 2)

In 30 ml of acetone was dissolved 3.6 g of the compound of Reference example 1, and by adding 7 ml of 2N-hydrochloric acid, the reaction was carried out at 50° C. for 3 hours. The solvent was removed under reduced pressure, and 100 ml of chloroform and 30 ml of a 10% potassium carbonate aqueous solution were added to the residue and the mixture was stirred. The chloroform layer was separated, dried over sodium sulfate, condensed and crystallized from chloroform-diethyl ether to give 2.4 g of the title compound. Melting point: 213° to 217° C. (decomposed).

EXAMPLE 53

Synthesis of N-(1,2,3,4-tetrahydroacridin-2-ol-9-yl)butanamide (Compound No. 8 in Table 1)

In 20 ml of methanol was dissolved 1 g of the compound of Example 52, and 0.14 g of sodium borohydride was added to the solution and reaction was carried out at room temperature for 12 hours. After removal of the solvent under reduced pressure, 30 ml of chloroform and 30 ml of water were added to the residue and the mixture was stirred. The chloroform layer was separated, dried over sodium sulfate and then condensed and crystallized from chloroform-ethyl acetate to give 0.77 g of the title compound. Melting point: 260° to 265° C. (decomposed).

REFERENCE EXAMPLE 2

Synthesis of 4-amino-5,6,7,8-tetrahydro thieno[2,3-6]-quinoline

In 45 ml of cyclohexanone were added 7.54 g of zinc chloride and 5.56 g of 2-amino-3-cyanothiophene and reaction was carried out at 100° to 110° C. for 2 hours.

After cooling the reaction system to 20° C., 20 ml of ethyl acetate was added thereto and crystals were filtered. These crystals were suspended in 100 ml of chloroform and the suspension was stirred by adding 17 ml of conc. aqueous ammonia. The chloroform solution was dried over sodium sulfate, condensed and crystallized from chloroform-n-heptane to give 6.11 g of the title compound. Melting point: 159° to 161° C.

REFERENCE EXAMPLE 3

Synthesis of 10-amino-1H-3,4-dihydro-pyrano[4,3-b]quinoline

By mixing 5.04 g of tetrahydro-4H-pyran-4-one and 8.92 g of zinc chloride with 5.95 g of 2-aminobenzonitrile, and the mixture was reacted at 90° C. for one hour. After cooling to room temperature, resulting solid was crushed by adding 20 ml of toluene and filtered. This solid was suspended in 180 ml of chloroform and the suspension was stirred by adding 22 ml of conc. aqueous ammonia. The chloroform solution was separated therefrom, dried over sodium sulfate, condensed and crystallized from chloroform-n-heptane to give 5.84 g of the title compound. Melting point: 199° to 202° C.

REFERENCE EXAMPLE 4

Synthesis of 4-amino-5H-7,8-dihydro-pyrano[4,3-b]thieno-[3,2-e]pyridine

In the same manner as in Reference example 3, the title compound was synthesized. Melting point: 199° to 202° C.

REFERENCE EXAMPLE 5

Synthesis of 10-amino-2-benzyl-1,2,3,4-tetrahydro-benzo[b][1,6]naphthylidine

In 400 ml of dimethylformamide were added 55 g of isatin, 76.2 g of N-benzyl-4-piperidone and 86.4 g of ammonium acetate and reaction was carried out at 120° C. for 3 hours. After removal of the solvent under reduced pressure, 200 ml of acetone and 200 ml of water were added to the residue and insolubles were collected by filtration. These insolubles were suspended in and washed with 400 ml of ethanol, and fitered to give 67.8 g of 2-benzyl-10-carbamoyl-1,2,3,4-tetrahydro-benzo[b][1,6]naphthylidine. Melting point: 234° to 237° C.

In 250 ml of water was dissolved 20.2 g of sodium hydr oxide, 22.2 g of bromine was added dropwise at −5° C. and then 40 g of carboxamide of the above compound was added thereto, and the mixture was elevated to 80° C. over 4 hours while thoroughly stirring. After cooling the mixture to 20° C., precipitated crystals were collected by filtration, washed and recrystallized from methanol to give 13 g of the title compound. Melting point: 193° to 196° C.

REFERENCE EXAMPLE 6

Synthesis of 10-amino-2-methyl-1,2,3,4-tetrahydro-benzo[b][1,6]naphthylidine

In the same manner as in Reference example 5, the title compound was synthesized. Melting point: 169° to 171° C.

REFERENCE EXAMPLE 7

Synthesis of 10-amino-2-methyl-1,3-propano-1,2,3,4-tetrahydro-benzo[b][1,6]naphthylidine By mixing 4.36 g of 2-aminobenzonitrile and 7 g of pseudopelletierine hydrochloride with 5.53 g of zinc chloride and the mixture was reacted at 150° C. for 2.5 hours. After cooling to room temperature, resulting solid was crushed by adding 10 ml of isopropanol and filtered. This solid was suspended in 100 ml of chloroform and the suspension was stirred by adding 22 ml of conc. aqueous ammonia. The chloroform solution was separated therefrom, condensed, purified through silica gel column chromatography (chloroform-methanol) and recrystallized from ethyl acetate to give 1.2 g of the title compound. Melting point: 220° to 240° C. (decomposed).

REFERENCE EXAMPLE 8

Synthesis of 4-amino-5,8-ethano-5,6,7,8-tetrahydro-thieno-[2,3-b][1,5] naphthylidine By mixing 5 g of 2-amino-3-cyanothiophene and 3-quinucridinone hydrochloride with 6.04 g of zinc chloride and the mixture was reacted at 110° C. for one hour. After cooling to room temperature, resulting solid was crushed by adding 100 ml of chloroform, and then 30 ml of conc. aqueous ammonia and 10 ml of methanol were added thereto and the mixture was stirred. Insolubles were removed by filtration, and the chloroform layer was separated therefrom, condensed, purified through silica gel column chromatography and recrystallized from ethyl acetate to give 0.59 g of the title compound. Melting point: 265° to 268° C. (decomposed).

TEST EXAMPLE 1

Effects on Na+dependent high-affinity choline uptake (HACU) of AF64A-treated rat hippocampus

Method

According to the method of Fischer et al. [J. Pharm. Exper. Ther., Vol. 222, p. 140 (1982)], AF64A was prepared from AF64. AF64A (1.5 nmole/1.5 µl/side) was injected into rat's both ventricles. After one week, subjecting decapitation, only hippocampus was taken out. It was homogenized with 0.32M of sucrose, centrifuged for 10 minutes at 1000 g, and the supernatant was further centrifuged for 20 minutes at 20,000 g to give crude synaptosomal fraction. The crude synaptosomal fraction and medicament were subjected to incubation at 37° C. for 30 minutes, and after addition of [$^3$H]choline (1 µM), they were further subjected to incubation at 37° C. for 10 minutes.

As a control, the crude synaptosomal fraction was subjected to incubation at 37° C. for 30 minutes, and after addition of choline [$^3$H]choline (1 µM), it was further subjected to incubation at 37° C. for 10 minutes to use. The reaction was stopped by subjecting filtration on Whatman GF/B filter. Radioactivity on the filter was measured by a liquid scintillation counter and it was made as the HACU amount. An amount of protein was determined according to the method of Bradford. [Analytical Biochemistry, Vol. 72, p. 248 (1976)]. The test results are shown in Table 9.

TABLE 9

| Example No. | Improved ratio (% based on Control) | | | | |
|---|---|---|---|---|---|
| | $10^{-8}$ M | $10^{-7}$ M | $10^{-6}$ M | $10^{-5}$ M | $10^{-4}$ M |
| 1 | 20** | 13** | 28** | 31** | 15 |
| 3 | 13* | 16** | 11* | 19* | 21* |
| 4 | 4 | 5 | 3 | 29* | 5 |
| 14 | 12 | 19 | 16 | 17** | 21 |
| 15 | 3 | −5 | 28 | −2 | — |
| 20 | 10 | 21* | 23** | 9 | 28* |
| 21 | 10 | 11 | 19* | 32** | 18* |
| 22 | 13* | 16 | 10 | 30* | 4 |
| 27 | 5 | 19* | 25** | 41** | 9 |
| 35 | 2 | 26 | 15 | 27** | 26 |
| 37 | 14 | 9 | 27** | 34** | 39** |
| 39 | 5 | 8 | 16** | 24* | −11** |
| 40 | 8 | 18 | 14 | 20 | 3 |
| 41 | 5 | 5 | 18 | 46** | 20 |
| 42 | 11 | 14 | 30* | 29** | 11 |
| 46 | −8 | 11 | 28 | 13 | 27* |
| 50 | 4 | 20* | 35** | 27 | −10 |
| 53 | 14 | 18 | 23 | 15 | 14 |
| Comparative+ | 2 | 5 | 8 | −11 | −73** |

Comparative+: 9-Amino-1,2,3,4-tetrahydroacridine
(*P < 0.05, **P < 0.01)

TEXT EXAMPLE 2

ACUTE TOXICITY TEST

The compound of the present invention was orally administered to a mouse and acute toxicity value was measured. The results are shown in Table 10.

TABLE 10

| Example No. of the compound | Acute toxicity value ($LD_{50}$ mg/kg) |
|---|---|
| 1 | 1000 |
| 14 | 2300 |
| 37 | 2100 |
| 9-Amino-1,2,3,4-tetrahydroacridine | 67 |

We claim:

1. A 9-acylamino-tetrahydroacridine derivative of the following formula (I):

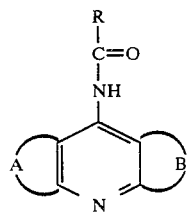

wherein:

R represents (i) a $C_{2-8}$ alkyl group, (ii)

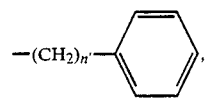

Wherein N' = 1 to 3 or (iii) a group of formula (II):

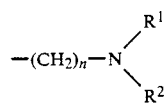

where $R^1$ represents a hydrogen atom or a $C_{1-6}$ alkyl group, $R^2$ represents a hydrogen atom,

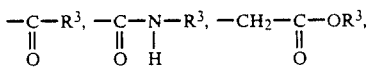

where $R^3$ is hydrogen or a $C_{1-6}$ alkyl group, or

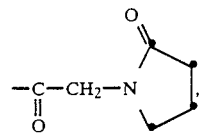

or $R^1$ and $R^2$ taken together with the nitrogen atom to which they are attached form

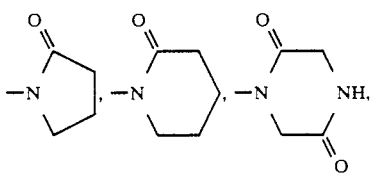

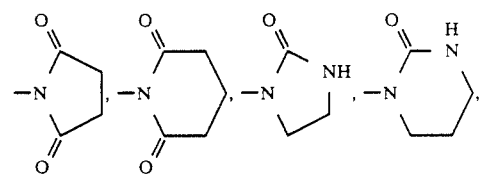

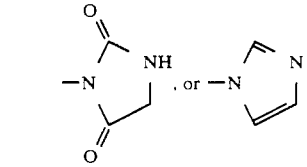

and n is 1 or 2;

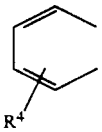

represents (i)

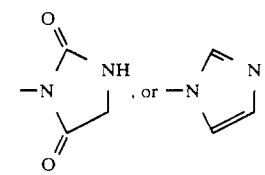

where $R^4$ is hydrogen, halogen, $C_{1-4}$ alkyl, alkoxy or hydroxyl; or (ii)

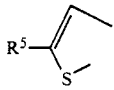

where $R^5$ is hydrogen or $C_{1-4}$ alkyl; and represents (i) 

(ii) 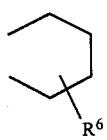

where R⁶ is hydrogen, $C_{1-4}$ alkyl or hydroxyl, (iii) 

(iv) 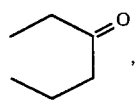

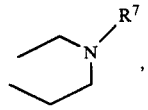

where R⁷ is hydrogen, $C_{1-4}$ alkyl, benzyl, phenethyl,

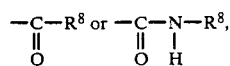

where R⁸ is hydrogen or $C_{1-6}$ alkyl, (v) 

(vi) 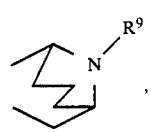

where R⁹ is hydrogen atom or $C_{1-6}$ alkyl, (vii)

(viii) 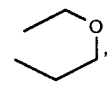

(ix) 

(x) 

or (xi) 

its optical antipode or pharmaceutically acceptable acid addition salt thereof.

2. The compound of claim 1, wherein said R group is the radical (iii) represented by formula (II).

3. The compound of claim 1, wherein said alkyl group of substituent R is ethyl, n-propyl, isopropyl, n-butyl, sec-butyl or t-butyl.

4. The compound of claim 1, wherein said alkyl group of substituents R¹ and R³ is methyl, ethyl, n-propyl, isopropyl, n-butyl or sec-butyl.

5. The compound of claim 1, wherein, of groups R⁴ to R⁷, said halogen is fluorine, chlorine, bromine or iodine, said alkyl is methyl, ethyl, n-propyl, isopropyl, n-butyl, or sec-butyl; said alkoxy group is methoxy, ethoxy, n-propoxy, isopropoxy, n-butoxy or sec-butoxy.

6. The compound of claim 1, wherein said

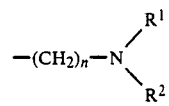

groups in the formula (II) of substituent R is

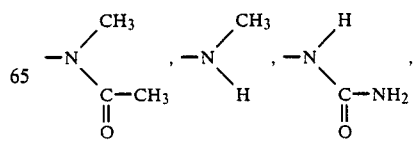

-continued

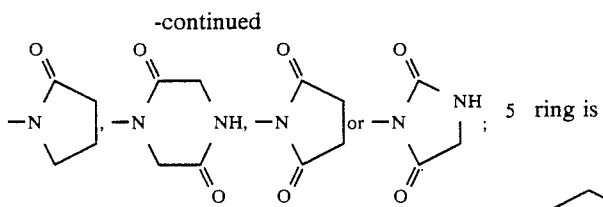

and N is 1.

7. The compound of claim 1, wherein said

ring is

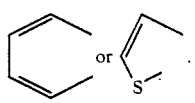

8. The compound of claim 1, wherein said ring is

9. A memory enhancing composition, comprising:
an effective amount of the 9-acylaminotetrahydroacridine derivative, its optical antipode or pharmaceutically acceptable acid addition salt thereof of claim 1 which activates a presynaptic site of the cholinergic neurons by increasing a high affinity choline uptake function to cholinergic neurons in combination with a pharmaceutically acceptable excipient.

10. A method of treating memory loss comprising:
administering to a subject an effective amount of the composition of claim 9.

* * * * *